United States Patent
Jin et al.

(10) Patent No.: US 8,114,279 B2
(45) Date of Patent: Feb. 14, 2012

(54) REMOVAL OF MICROORGANISMS AND DISINFECTION BYPRODUCT PRECURSORS USING ELEMENTAL IRON OR ALUMINUM

(75) Inventors: Yan Jin, Newark, DE (US); Pei Chiu, Hockessin, DE (US)

(73) Assignee: University of Delaware, Newark, DE (US)

( * ) Notice: Subject to any disclaimer, the term of this patent is extended or adjusted under 35 U.S.C. 154(b) by 200 days.

(21) Appl. No.: 11/375,206

(22) Filed: Mar. 15, 2006

(65) Prior Publication Data

US 2006/0249465 A1  Nov. 9, 2006

Related U.S. Application Data

(63) Continuation-in-part of application No. PCT/US2004/030025, filed on Sep. 15, 2004.

(60) Provisional application No. 60/503,266, filed on Sep. 15, 2003.

(51) Int. Cl.
*C02F 1/50* (2006.01)
*C02F 1/28* (2006.01)

(52) U.S. Cl. ............. 210/192; 210/198.1; 210/205; 210/209; 210/282; 210/290; 210/501; 210/502.1

(58) Field of Classification Search .......... 210/192
See application file for complete search history.

(56) References Cited

U.S. PATENT DOCUMENTS

| | | | | |
|---|---|---|---|---|
| 4,178,249 A * | 12/1979 | Councill | ........ | 210/281 |
| 5,149,437 A * | 9/1992 | Wilkinson et al. | ........ | 210/665 |
| 5,178,768 A * | 1/1993 | White, Jr. | ........ | 210/663 |
| 5,198,118 A * | 3/1993 | Heskett | ........ | 210/638 |
| 5,298,720 A * | 3/1994 | Cuomo et al. | ........ | 219/121.43 |
| 5,432,077 A * | 7/1995 | Farrah | ........ | 435/244 |
| 5,795,471 A * | 8/1998 | Naito | ........ | 210/223 |
| 5,833,859 A | 11/1998 | Heskett | | |
| 5,935,609 A * | 8/1999 | Denkewicz et al. | ........ | 424/618 |
| 6,132,623 A | 10/2000 | Nikolaidis et al. | | |
| 6,221,262 B1 * | 4/2001 | MacDonald et al. | ........ | 210/757 |
| 6,280,625 B1 | 8/2001 | Jackson, Jr. et al. | | |
| 6,387,276 B1 | 5/2002 | Nikolaidis et al. | | |
| 6,861,002 B2 * | 3/2005 | Hughes | ........ | 210/681 |
| 6,942,807 B1 * | 9/2005 | Meng et al. | ........ | 210/719 |
| 6,994,792 B2 * | 2/2006 | Schlegel | ........ | 210/660 |
| 7,156,994 B1 * | 1/2007 | Archer | ........ | 210/266 |
| 7,614,506 B2 * | 11/2009 | Mitchell et al. | ........ | 210/506 |

(Continued)

FOREIGN PATENT DOCUMENTS

WO   WO 03/078030   9/2003

(Continued)

OTHER PUBLICATIONS

European Search Report, Application No. EP04784023. dated Apr. 28, 2009.

(Continued)

*Primary Examiner* — Peter A Hruskoci
(74) *Attorney, Agent, or Firm* — Potter Anderson Corroon LLP (57) ABSTRACT

A process for removing microorganisms and/or precursors of disinfection by-products from a medium sought to be treated comprising treating the medium with one or more elements capable of forming an oxide, a hydroxide, and/or an oxyhydroxide through corrosion is disclosed. A system for effecting the removal or inactivation of microorganisms and/or disinfection by-product precursors is also contemplated.

13 Claims, 6 Drawing Sheets

U.S. PATENT DOCUMENTS

| | | | |
|---|---|---|---|
| 2001/0054588 A1 | 12/2001 | Smith | |
| 2003/0146169 A1 | 8/2003 | Ciampi et al. | |
| 2003/0173306 A1* | 9/2003 | Cha et al. | 210/743 |
| 2005/0252862 A1 | 11/2005 | Gaid | |

FOREIGN PATENT DOCUMENTS

| | | |
|---|---|---|
| WO | WO 03/089112 | 10/2003 |
| WO | WO 2004/002605 | 1/2004 |

OTHER PUBLICATIONS

Ryan et al., Field and Laboratory Investigations of Inactivation of Viruses . . . , Environmental Sci. & Tech., XP009115944, vol. 36, pp. 2403-2413, 2002.

Alowitz, M.J. et al., "Kinetics of Nitrate, Nitrite, and Cr(VI) Reduction by Iron Metal", Environmental Science & Technology, vol. 36, No. 3, 2002, pp. 299-306.

Arnold, W.A. et al., "Polychlorinated ethane reaction with zero-valent zinc: pathways and rate control", Journal of Contaminant Hydrology, vol. 40, (1999), pp. 183-200.

Farrell, J. et al., "Electrochemical and Spectroscopic Study of Arsenate Removal from Water Using Zero-Valent Iron Media", Environmental Science Technology, (2001), vol. 35, pp. 2026-2032.

Gerba, C.P. et al., "Quantitative Assessment of the Adsorptive Behavior of Viruses to Soils", Environmental Science & Technology, vol. 15, pp. 940-944, Aug. 1981.

Gu, B. et al., "Adsorption and Desorption of Natural Organic Matter on Iron Oxide: Mechanisms and Models", Environmental Science Technology, (1994), vol. 28, pp. 38-46.

Hozalski, R.M. et al., "Reduction of Haloacetic Acids by $Fe^0$: Implications for Treatment and Fate", Environmental Science Technology, (2001), vol. 35, pp. 2258-2263.

Jarvis, P. et al., "How the Natural Organic Matter to Coagulant Ratio Impacts on Floc Structural Properties", Environmental Science Technology (2005), vol. 39, pp. 8919-8924.

Jensen, J.S. et al., "Rates of Reduction of N-Chlorinated Peptides by Sulfite: Relevance to Incomplete Dechlorination of Wastewaters", Environmental Science Technology, (1998), vol. 32, pp. 516-522.

Maccrehan, W.A. et al., <<Detection of Sewage Organic Chlorination Products That are Resistant to Dechlorination with Sulfite, Environmental Science Technology, (1998), vol. 32, pp. 3640-3645.

Melitas, N. et al., "Electrochemical Study of Arsenate and Water Reduction on Iron Media Used for Arsenic Removal from Potable Water", (2002), vol. 36, pp. 3188-3193.

Melitas, N. et al., "Understanding Soluble Arsenate Removal Kinetics by Zerovalent Iron Media", Environmental Science Technology, (2002), vol. 36, pp. 2074-2081.

Moore, R.S. et al., "Poliovirus Adsorption by 34 Minerals and Soils", Applied and Environmental Microbiology, Dec. 1981, vol. 42, No. 6, pp. 963-975.

Murray, J.P. et al., "Degradation of Poliovirus by Adsorp ion on Inorganic Surfaces", Applied and Environmental Microbiology, Mar. 1979, vol. 37, No. 3, pp. 480-486.

Odziemkowski, M.S. et al., "Mechanism of Oxide Film Formation on Iron in Simulating Groundwater Solutions: Raman Spectroscopic Studies", Corrosion Science, vol. 40, No. 2/3, pp. 371-389, (1998).

Oh, S.Y. et al., "Enhancing Fenton oxidation of TNT and RDX through pretreatment with zero-valent iron", Water Research, vol. 37, (2003), pp. 4275-4283.

Perey, J.R. et al., "Zero-Valent Iron Pretreatment for Enhancing the Biodegradability of Azo Dyes", Water Environment Research, vol. 74, No. 3, pp. 221-225, May/Jun. 2002.

Plewa, M.J. et al., "Chemical and Biological Characterization of Newly Discovered Iodoacid Drinking Water Disinfection Byproducts", Environmental Science & Technology, vol. 38, No. 18, (2004) pp. 4713-4722.

Ryan, J.N. et al., "Field and Laboratory Investigations of Inactivation of Viruses (PRD1 and MS2) Attached to Iron Oxide-Coated Quartz Sand", Environmental Science & Technology, vol. 36, No. 11, (2002), pp. 2403-2413.

Sagripanti, J.L., "Metal-Based Formulations with High Microbicidal Activity", Applied and Environmental Microbiology, vol. 58, No. 9, Sep. 1992, pp. 3157-3162.

Sagripanti, J.L. et al., "Virus Inactivation by Copper or Iron Ions Alone and in the Presence of Peroxide", Applied and Environmental Microbiology, Dec. 1993, vol. 59, No. 12, pp. 4374-4376.

Su, C. et al., "In Situ Remediation of Arsenic in Simulated Groundwater Using Zerovalent Iron: Laboratory Column Tests on Combined Effects of Phosphate and Silicate", Environmental Science Technology, (2003), vol. 37, pp. 2582-2587.

United States Environmental Protection Agency, 2000, "National Primary Drinking Water Regulations: Ground Water Rule", Proposed Rule, Federal Register, vol. 65, No. 91, pp. 30193-30274.

United States Environmental Protection Agency, "Field Applications of in Situ Remediation Technologies: Permeable Reactive Barriers", Washington DC, Jan. 2002.

Wilkin, R.T. et al., Long-term Performance of Permeable Reactive Barriers Using Zero-valent Iron: An Evaluation at Two Sites, United States Environmental Protection Agency Environmental Research Brief, EPA/600/S-02/001, Mar. 2002.

Vidic, R.D., "Permeable Reactive Barriers: Case Study Review", Ground-Water Remediation Technologies Analysis Center, TE-01-01, Nov. 2001.

Payment, P. et al., "A prospective epidemiological study of gastrointestinal health effects due to the consumption of drinking water", International Journal of Environmental Health Research, vol. 7, pp. 5-31, (1997).

Chu, Y. et al., "Virus Transport through Saturated Sand Columns as Affected by Different Buffer Solutions", Journal of Environmental Quality, vol. 29, No. 4, Jul.-Aug. 2000, pp. 1103-1110.

McMurry, S.W. et al., "Fecal Coliform Transport through Intact Soil Blocks Amended with Poultry Manure", Journal Environ. Qual., vol. 27, pp. 86-92, (1998).

Abbaszadegan, M. et al., "Occurrence of Viruses in US Groundwaters", Journal AWWA, vol. 95, No. 9, Sep. 2003, pp. 107-120.

Gerba, C.P. et al., "Viruses in Source and Drinking Water", Drinking Water Microbiology, Chapter 18, pp. 380-396.

Kramer, M.H. et al., << Waterborne disease : 1993 and 1994 >>, Journal AWWA, pp. 66-80.

Kunze, G.W. et al., << Pretreatment for Mineralogical Analysis, American Society of Agronomy. pp. 92-100, Chapter 5.

Payment, P. et al., "A Randomized Trial to Evaluate the Risk of Gastrointestinal Disease due to consumption of Drinking Water Meeting Current Microbiological Standards", American Journal of Public Health, vol. 81, No. 6, Jun. 1991, pp. 703-708.

Jin, Y. et al., "Fate and Transport of Viruses in Porous Media", Advances in Agronomy, vol. 77, pp. 39-102.

Payment, P. et al., "Virus Removal by Drinking Water Treatment Processes", Critical Reviews in Environmental Control, vol. 19, Issue 1, (1989) pp. 15-31.

Zerda K.S., "Adsorption of Viruses to Charge-Modified Silica", Jun. 1982, pp. 1-128.

Rosenberger, J.K. et al., "Viral Arthritis/Tenosynovitis and other Reovirus Infections", American Association of Avian Pathologists, pp. 207-210, Chapter 38.

Hancock, C.M. et al., "Crypto and Giardian in US groundwater", Journal Awwa, vol. 90, Issue 3, pp. 58-61, Mar. 1998.

Adams, M.H., "Bacteriophages", Interscience Publishers, Inc., (1959), pp. 27-34.

Bull, R.J. et al., "Evaluation of the Health Risks Associated with Disinfection", vol. 20, Issue 2, (1990), pp. 77-113.

Yates, M.V. et al., "Virus Persistence in Groundwater", Applied and Environmental Microbiology, vol. 49, No. 4, Apr. 1985, pp. 778-781.

Dunn, J.V. et al., "Single-Stranded RNA Phages", The Bacteriophages-Second Edition, pp. 175-196, Chapter 15.

Schroth, M.H. et al., "Characterization of Miller-Similar Silica Sands for Laboratory Hydrologic Studies", Soil Science Society American Journal, vol. 60, pp. 1331-1339, (1996).

Korich, D.G. et al., "Effects of Ozone, Chlorine Dioxide, Chlorine, and Monochloramine on *Cryptosporidium parvum* Oocyst Viability", Applied & Environmental Microbiology, vol. 56, No. 5, May 1990, pp. 1423-1428.

Mead, P.S. et al., << Food-Related Illness and Death in the United States >>, Emerging Infectious Diseases, vol. 5, No. 5, Sep.-Oct. 1999, pp. 607-625.

Harriott, P., "Mass Transfer to Particles: Part 1. Suspended in Agitated Tanks", A.I.Ch.E. Journal, vol. 8, No. 1, pp. 93-101, Mar. 1962.

Chu, Y. et al., "Mechanisms of virus removal during transport in unsaturated porous media", Water Resources Research, vol. 37, No. 2, pp. 253-263, Feb. 2001.

Jin, Y. et al., "Sorption of Viruses during Flow through Saturated Sand Columns", Environmental Science Technology, (1997), vol. 31, pp. 548-555.

Jin, Y. et al., "Virus removal and transport in saturated and unsaturated sand columns", Journal of Contaminant Hydrology, vol. 43, (2000), pp. 111-128.

Penrod, S.L. et al., Deposition Kinetics of Two Viruses in Packed Beds of Quartz Granular Media >>, Langmuir, (1996), vol. 12, pp. 5576-5587.

Vaughn, J.M. et al., "Survey of Human Virus Occurrence in Wastewater-Recharged Groundwater on Long Island", Applied & Environmental Microbiology, vol. 36, No. 1, Jul. 1978, pp. 47-51.

Wilke, C.R. et al., Correlation of Diffusion Coefficients in Dilute Solution, A.I.Ch.E. Journal, Jun. 1955, pp. 264-270.

Lee et al.., Bactericidal Effect of Zero-Valent Iron Nanoparticles on *Escherichia coli*, Environ. Sci. Technol. 2008, 42, 4927-4933.

Auffan et al., Relation between the Redox State of Iron-Based Nanoparticles and Their Cytotoxicity toward *Escherichia coli*, Environ. Sci. Technol. 2008, 42, 6730-6735.

T. Bryant, UD drinking-water technology named one of year's top advances, http://www.udel.edu/PR/UDaily/2008/dec/nasa120707.html.

PHI X 174—Wikipedia, the free encyclopedia, 1 page, Nov. 11, 2009.

*Pseudomonas* —Wikipedia, the free encyclopedia, 8 pages, last modified Dec. 2, 2009.

*Escherichia Coli* —Wikipedia, the free encyclopedia, 13 pages, last modified Dec. 8, 2009.

*Kobuvirus* —Wikipedia, the free encyclopedia, 2 pages, last modified Nov. 12, 2009.

Tobacco mosaic virus—Wikipedia, the free encyclopedia, 4 pages, last modified Nov. 23, 2009.

*Adenoviridae* —Wikipedia, the free encyclopedia, 6 pages, last modified Nov. 5, 2009.

Hoch et al., Carbothermal Synthesis of Carbon-supported Nanoscale Zero-valent Iron Particles for the Remediation of . . . , Environ. Sci. Technol. 2008, 42, 2600-2605.

Zheng et al.,Reactivity Characteristics of Nanoscale Ze rovalent Iron-Silica Composites for . . . , Environ. Sci. Technol. 2008, 42, 4494-4499.

Li et al., Debromination of Decabrominated Diphenyl Ether by Resin-Bound Iron Nanoparticles, Environ. Sci. Technol. 2007, 41, 6841-6846.

Choi et al., Synthesis of Reactive Nano-Fe/Pd Bimetallic System-Impregnated Activated Carbon for the Simultaneous ..PCBs, Downloaded from http:http://pubs.acs.org on Apr. 20, 2009.

How copper-zinc water treatment systems work, Article, 3 pages.

Waterborne diseases—Wikipedia, the free envyclopedia, 7 pages, modified Jan. 11, 2010.

* cited by examiner

REMOVAL OF MICROORGANISMS AND DISINFECTION BYPRODUCT PRECURSORS USING ELEMENTAL IRON OR ALUMINUM

CROSS-REFERENCE TO RELATED CASES

This application is a continuation-in-part of PCT application published on Mar. 31, 2005, as WO 2005/028378, which claims the U.S. and claims priority from U.S. Provisional Application Ser. No. 60/503,266, filed Sep. 15, 2003, the contents of which are incorporated herein by reference in their entirety.

STATEMENT REGARDING FEDERALLY SPONSORED RESEARCH

This study was supported in part by the United States Department of Agriculture (USDA) under research grant USDA-NRI #2001-01235. In consequence, the federal government may have certain rights in the invention.

BACKGROUND OF THE INVENTION

1. Field of the Invention

The present invention relates generally to media treatment processes and more specifically, to processes used to remove pathogens from water or wastewater.

2. Description of Related Art

Microorganisms pathogenic to humans are ubiquitous in the water cycle and have been found in drinking water and wells (Goyal et al., 1984; Gerba and Rose, 1990; Kramer et al., 1996). Major groups of microbial pathogens include viruses, bacteria, and protozoa. Sources of microbial contamination include, but are not limited to, leaking septic tanks and sewer lines, wastewater discharge and reuse, landfills, and sewage sludge application on land (Yates et al., 1985), as well as runoff and infiltration from animal waste-amended fields (McMurry et al., 1998). The USEPA Science Advisory Board cited drinking water contamination as one of the highest-ranking environmental risks and reported that microbial contaminants (e.g., bacteria, protozoa, and viruses) are likely to be the greatest remaining health risk management challenge for drinking-water suppliers (USEPA, 1990). Types of illness that can result from exposure to microbial pathogens range from mild or moderate cases lasting a few days to more severe infections that last several weeks and may result in death in the more sensitive subpopulations (e.g., young children, elderly, and people with compromised immune systems). A major study of the occurrence of pathogens in U.S. ground waters tested samples collected from 448 sites in 35 states for various indicators of fecal contamination (total coliform, *E. coli*, somatic and male-specific coliphages, and human viruses) (Abbaszadegan et al., 2003). It was found that 31.5% of the samples were positive for one or multiple pathogenic viruses using polymerase chain reaction (PCR), and human viruses were detected in 4.8% of the samples by cell culture.

Concerns over the number of waterborne disease outbreaks that continue to occur in the U.S. despite improvements in drinking water treatment practices, have resulted in the development of regulations to reduce such risks. The Surface Water Treatment Rule (SWTR) (USEPA, 1989a) and Interim Enhanced SWTR (USEPA, 1989b) were established in an effort to control microbial contaminants in drinking water systems using surface water or groundwater under direct influence of surface water. In addition, the EPA recently proposed a Ground Water Rule (GWR). The GWR is aimed at addressing microbial contamination of ground water-supplied drinking water systems in accordance with the Safe Drinking Water Act (SDWA) of 1974, as amended in 1986 and again in 1996 (USEPA, 2000). The GWR and other regulations address microbial contamination and DBP formation in drinking water systems in order to reduce public health risks resulting from pathogenic contamination and DBP toxicity. The 1986 SDWA amendments directed the EPA to establish national primary drinking water regulations requiring disinfection as treatment for the inactivation of microbiological contaminants for all public water systems, including systems supplied by ground water sources. Worldwide, there is a great interest to redirect investments in water infrastructure to cheap, decentralized, and environmentally sustainable technologies to meet the demand for water and energy in developing countries. The United Nation's Millennium Development Goal is to bring 100 million small farming families out of extreme poverty through low-cost water technologies in the next 10 years. Furthermore, technologies with greater efficiencies than chlorine or iodine to remove microbial agents from water will significantly improve the effectiveness of portable water treatment devices. In the last decade, zero-valent iron has been increasingly used as a reactive material in permeable reactive barriers (PRBs) to remediate groundwater contaminated with solvents and other organic, metallic, and radioactive chemicals.

Although viruses are only one type of microbial pathogen known to contaminate groundwater, they are much smaller than bacteria and protozoan cysts, and thus are filtered out to a much smaller extent in porous media than bacteria due to their size. Therefore viruses can travel much longer distances in the subsurface (Jin and Flury, 2002). Viruses are identified as the target organisms in the GWR because they are responsible for approximately 80% of disease outbreaks for which infectious agents were identifiable (Ryan et al., 2002). In addition to viruses, the protozoan parasite *Cryptosporidium* is another waterborne pathogen of significant public health concern. Survey studies have found oocysts in 4-100% of surface water samples examined, with concentrations up to 10,000 oocysts per 100 L of water. (Lisle et al., 1995). Groundwater may also contain oocysts as shown by a 22% prevalence rate in one study performed in the U.S. (Hancock et al., 1998). The difficulty in controlling cryptosporidiosis is due in part to the resistance of *Cryptosporidium* oocysts to commonly used levels of disinfectants in drinking and recreational waters. (Korich et al., 1990).

Disinfection is an important water treatment process for preventing the spread of infectious diseases. While mostly effective for removing many bacteria, classical disinfectants such as chlorine have been shown as not always being sufficiently effective against viruses and protozoa (Payment and Armon, 1989; Bull et al., 1990).

Data collected by the Centers for Disease Control and Prevention (CDC) and the EPA indicate that almost as many waterborne disease outbreaks were reported between 1971 and 1996 in systems with disinfection treatment that was inadequate or interrupted (134 outbreaks) as were reported in the same period among systems that did not disinfect (163 outbreaks) (USEPA, 2000). High doses of chlorine also can produce excessive amounts of disinfection by-products (DBPs) through reaction with DBP precursors such as natural organic matter in source water. More than 500 DBPs have been identified (Plewa et al., 2004). The most commonly reported, and currently regulated, chlorination DBPs include total trihalomethanes (TTHM: chloroform, bromodichloromethane, dibromochloromethane, and bromoform) and haloacetic acids (HAA5, monochloroacetic, dichloroacetic, trichloroacetic, monobromoacetic and dibromoacetic acids). Many of these DBPs are known or suspected human carcinogens and have been linked to bladder, rectal, and colon cancers (U.S. EPA, 2003a and b). Studies on human epidemiology and animal toxicology have also demonstrated links between chlorination of drinking water and reproductive and developmental effects, such as fetal losses and neural tube and heart defects (U.S. EPA 2003b). It has been estimated that about 254 million Americans are exposed to DBPs, and the U.S. EPA is proposing the Stage 2 Disinfection Byproduct Rule (U.S. EPA, 2003c), which is aimed at protecting public health from DBPs in water. Consequently, it is increasingly recognized that removal of natural organic matter during water treatment is critical for minimizing formation of DBPs in drinking water (Jarvis et al., 2005).

Although strongly oxidizing disinfectants other than chlorine, such as chloramines, ozone, and chlorine dioxide, are being used in the U.S. and Europe, and alternative non-oxidant-based disinfection methods such as ultraviolet (UV) irradiation and membrane processes are available, these options are often more expensive in terms of capital investment and operation cost and/or complex and thus difficult to implement. In addition, some of the non-chlorine disinfection alternatives also generate DBPs, which can include bromate.

In addition to drinking water treatment, wastewater discharge and reuse (e. g., through groundwater recharge and irrigation) and land-application of sewage sludge have attracted increasing public attention and growing concern because of the presence of human and animal pathogens in treated wastewater and sludge. Because wastewater treatment generally includes primary and secondary treatment, which may only remove a fraction of the pathogenic microorganisms, discharge of treated wastewater and sludge represent a potential source of microbial contamination. In addition, chlorination and dechlorination (often with sulfur dioxide or sulfite salts) of treated wastewater prior to its discharge not only adds to the treatment cost but also generates undesirable DBPs including THMs, HAAs, and N-nitrosamines that are highly toxic to aquatic organisms (Jensen and Helz, 1998; MacCrehan et al., 1998).

The Department of Homeland Security has reported that water treatment facilities that use chlorine are more attractive targets for terrorist attack. A major failure of chlorine storage tanks could produce a chlorine gas plume that would affect residents within a ten-mile radius. Currently about 600 facilities could threaten between 10,000 and 100,000 people (U.S. DHS, 2003). In addition, accidental release of chlorine gas may have catastrophic consequences. Moreover, some chlorine-manufacturing facilities still use mercury cell electrolysis, a process that can release large quantities of mercury into the environment. If a safer, non-oxidant-based disinfection method is used in a treatment facility to provide additional removal of microbial pathogens, the consumption, transport, and on-site storage of chlorine may be reduced, thus minimizing our dependence on chlorine and the risks associated with the chlorine infrastructure.

One of the most complex problems facing the water industry today is how to provide adequate protection against infectious diseases without the risk from disinfectants and DBPs. It is difficult to manage both microbial and DBP risks, and even more challenging to do so at an acceptable cost. With increasing population and growing demand for potable water, increasingly stringent environmental regulations, and heightened security concerns, developing innovative, inexpensive, and robust technologies that can simultaneously reduce the risks of pathogens, DBPs, and residual disinfectants in drinking water is of utmost urgency.

Portable drinking water systems or chemical additives are available for household use, traveling to remote areas including earthbound and outer space, recreation including camping and hiking, humanitarian purposes, military and engineering operations in remote areas, and disaster relief where water supplies are interrupted. Effective additives for pathogen removal that are currently used in those devices include chlorine, chlorine dioxide, and iodine. However, although chlorine and iodine are effective for removal of bacteria, they are limited in effectiveness against viruses and protozoa (e.g. *Cryptosporidium* and *Giardia*.)

In the last decade, elemental iron (a. k. a. zero-valent iron, metallic iron, Fe(0), and iron metal) has been increasingly used as a reactive material in permeable reactive barriers (PRBs) to remediate groundwater contaminated with solvents and other organic, metallic, and radioactive chemicals (Vidic, 2001; EPA 2002a). PRBs are subsurface treatment zones that contain reactive materials, such as elemental iron, placed in the flow path of contaminated groundwater. PRBs have higher permeability than adjacent aquifer materials and, as groundwater flows through the PRB, dissolved contaminants are removed from water through physical and chemical processes such as adsorption, reduction reactions, and precipitation. Since 1995, more than 120 field-scale PRBs have been installed worldwide, most of them in the U.S. and Europe (RTDF, 2003; ETI, 2005).

Approximately 80% of the PRBs contain elemental iron, typically in the form of inexpensive commercial iron filings (EPA, 2002a). Unlike the conventional pump-and-treat method, PRBs are in situ and passive and involve minimal maintenance and operation costs. Iron PRBs also have long service lives and have been shown to remove and/or degrade pollutants effectively and continuously for multiple years (EPA, 2002a, b).

In addition to its use in PRBs for groundwater remediation, iron was evaluated for water and wastewater treatment in recent years. It has been shown that elemental iron could be used to treat wastewaters containing refractory compounds such as azodyes, nitroaromatic compounds, and explosives (Perey et al., 2002; Oh et al., 2003). It has also been demonstrated that reductive treatment with iron rapidly converts certain refractory compounds into products that are much more degradable in the subsequent chemical or biological oxidation processes (Perey et al., 2002; Oh et al., 2003).

Furthermore, elemental iron has also been shown to remove arsenic and other chemical pollutants from water (Farrell et al., 2001; Melitas et al., 2002). These authors reported that corrosion of iron continuously generates iron oxides to adsorb and remove arsenic from water. In December 2003, Sengupta of Lehigh University reported that the use of polymeric ion exchange beads impregnated with ferric hydroxide could be used to remove arsenic from well water in India.

The present invention addresses above-described problems of biological agents and DBPs in water and provides solutions thereto.

SUMMARY OF THE INVENTION

The invention is broadly related to purification of a fluid medium. The medium can include, but is not limited to, a liquid.

In a particular aspect, the invention comprises a process for removing and/or inactivating biological agents and/or precursors of disinfection by-products from a medium sought to be treated comprising treating the medium with one or more elements capable of forming an oxide, hydroxide, and/or oxyhydroxide through corrosion. In a particular aspect, the process occurs in a conduit or container. The process can be a water purification process. In one aspect, the process is carried out in a water treatment plant or a portable unit.

In another aspect, the invention comprises use of elemental iron and/or aluminum to remove and/or inactivate water borne and/or airborne biological agents, including, but not limited to, viruses, bacteria, protozoa, algae, fungi, and prions. The invention is also directed to methods for the removal of precursors of disinfection by-products (DBPs). This invention may be used to treat any material, and is particularly suitable for treating liquids such as water, including drinking water, wastewater, surface water, groundwater, backwash water, irrigation water, food-processing water, ballast water, leachate, medical waste, laboratory waste, pharmaceutical waste, or other aqueous waste. This invention is also suitable for treating air and other gases.

In another aspect, the invention is related to a disinfection system capable of being used to reduce biological agents in water or other media, comprising either a conduit packed with filtration media and at least one microorganism-removing agent, or a container comprising at least one microorganism-removing agent and water wherein said at least one microorganism-removing agent is selected from the group consisting of elements capable of forming an oxide, hydroxide, and/or oxyhydroxide through corrosion in water.

In yet another aspect, the invention comprises a disinfection product comprising a conduit, and within said conduit, at least one filtration medium and a microorganism-removing agent packed in said conduit wherein said microorganism-removing agent is present in an amount of from about 0.01 to about 99.99% based on the weight of the filtration medium, wherein said microorganism-removing agent comprises one or more agents capable of forming an oxide, hydroxide, and/ or oxyhydroxide through corrosion in water.

Additional objects, features, and advantages of the invention will be set forth in the description which follows, and in part, will be obvious from the description, or may be learned by practice of the invention. Objects, features and advantages of the invention may be realized and obtained by means of the instrumentalities and combination particularly pointed out in the appended claims.

BRIEF DESCRIPTION OF THE DRAWINGS

FIGS. 3($a$) and ($b$) shows the breakthrough curves of two viruses, $\phi$X174 (a) and MS2 (b), from columns packed with only oxide-removed (cleaned) sand vs. oxide-removed sand plus three millimeters of embedded elemental iron particles (in the form of commercial iron granules), over 37 pore volumes (i. e., the volume of virus-laded solution treated in this demonstration was 37 times that of the total void space in the column).

DETAILED DESCRIPTION OF PREFERRED EMBODIMENTS

Elemental iron or other elements such as aluminum, or combinations thereof can be used to remove microorganisms and/or other biological agents from water because elemental iron and other metallic elements can continuously generate and renew the surface oxides and oxyhydroxides through corrosion in water, and metal oxides and oxyhydroxides can remove and/or inactivate biological agents such as viruses. In accordance with the present invention, the term "microorganism-removing agent" means any element or combination of elements in any form that are capable of forming a metal oxide, hydroxide, and/or oxyhydroxide through corrosion. The terms "microbe," "microorganism," "microbial agent," "microbiological agent," and "biological agent" are interchangeably used throughout the instant disclosure and connote a living organism or non-living biological agent typically too small to be seen with the naked eye; including bacteria, fungi, protozoa, and microscopic algae; also includes viruses and prions. In accordance with the present invention, it was found that even a very thin layer (e. g., about 3 mm) of elemental iron particles (used as the microorganism-removing agent) in the flow path of virus- (or other) contaminated water (8.8 min residence time) resulted in approximately 2-log (99%) removal of two viruses over 40 pore volumes, and more than 90% of the removal was due to inactivation and/or irreversible sorption. Moreover, when a 7 cm thick iron/sand (1:1) layer was used, such that the residence time was about 20 min, the removal efficiency was over 5-log removal of the two test viruses. Results of the study using iron and two viruses support the invention that elements such as iron are capable of removing and/or inactivating microorganisms such as viruses.

As shown infra, results indicate that both MS2 and $\phi$X174 were significantly removed from solution after pumping the water through the zero-valent iron column. The more zero-valent iron that was used, the more viruses that were removed. Removal efficiencies for viruses can be about $3\text{-log}_{10}$ (99.9%), about $4\text{-log}_{10}$ (99.99%), about $5\text{-log}_{10}$ (99.999%), or even higher. In addition to the amount of iron, flow velocity may also affect the removal efficiency in some cases. Namely, a slower flow velocity can result in a higher removal efficiency. Mass balance results suggest that the removal of viruses is primarily due to inactivation or irreversible sorption. In accordance with the present invention, zero-valent iron can be employed for the treatment of microbially contaminated aqueous media, including drinking water, wastewater, groundwater, backwash water, irrigation water, ballast water, food-processing water, leachate, and other aqueous wastes such as medical wastes, and gaseous media including pathogen-laden air streams and process off-gases. In addition, processes of the present invention are also potentially useful for removal of prions, which may cause, for example, mad cow disease. Prions are nanometer-size protein particles that are biological in nature. Since elemental iron (through corrosion and oxide/oxyhydroxide formation) can remove viruses, which consist of a protein sheath, iron is expected to also be effective in removing prions. In addition, processes of the present invention are also useful for the removal of DBP precursors such as natural organic matter including humic acid and fulvic acid, as these DBP precursors are known to adsorb to metal oxides (Stumm and Morgan, 1996) and thus can be removed with elemental iron or other metals.

Elemental iron corrodes in water; that is, it is oxidized by dissolved oxygen, other oxidants in water, and water itself. Any element or combination of elements that corrodes in water may be useful in some embodiments of the present invention.

Iron corrosion generates minerals such as iron oxides, hydroxides, and oxyhydroxides (e. g., goethite and magnetite) on the surface, and iron oxides, hydroxides, and oxyhydroxides are capable of removing microorganisms from water. The mechanisms of removal may involve adsorption of microbial particles (e. g., viruses and bacteria) in water to iron surfaces through electrostatic attraction and/or other interactions. Aluminum functions in the same way by forming an aluminum oxide and hydroxides on the surface, and these aluminum corrosion products remove microorganisms from water. Iron and aluminum oxides and oxyhydroxides contain abundant positively charged surface sites because these minerals typically have a zero point of charge ($pH_{zPc}$) at circumneutral or alkaline pH, whereas most bacteria and viruses are negatively charged at neutral pH and therefore are attracted to the metal surface. Since iron corrodes to form new surface sites continuously in water and other aqueous media, iron can be used to remove viruses for as long as the corrosion continues. This can be multiple years, as has been demonstrated in many field-scale iron PRBs.

Thus, iron may be preferable in some cases although use of aluminum and other corrodible metals is also possible. When water containing microbes (such as viruses and bacteria) and DBP precursors (such as humic acid) comes into contact with elemental iron or aluminum particles (for example, in a treatment column or filter media), corrosion products of iron or aluminum will be generated constantly and microbes and DBP precursors can be removed from water in a continuous fashion.

As used herein, iron and/or aluminum are referred to specifically and such reference also includes other materials that will corrode to remove microorganisms and/or DBP precursors or other materials.

The present invention is useful, for example, in water treatment plants producing drinking water. Water can be treated in a treatment column, cartridge, or filter containing elemental iron (in the form of filings, shavings, or granules of pure, cast, gray, or scrap iron, for example) as an active component to remove microorganisms and/or DBP precursors in the water. Alternatively, iron or aluminum particles (and/or other corrodible metals) may be applied to treat water in a reactor, such as a mixed tank reactor or a batch reactor, to remove microbes, DBP precursors, and other undesirable materials from the water. Similar applications for the removal of microorganisms and/or DBP precursors from other aqueous (such as wastewater and groundwater) and gaseous media (such as air and off gases) are also envisioned. The present invention provides substantial benefits over other standard treatment options as it provides an effective, inexpensive, simple, and flexible method for removing virtually any type of microorganisms. In addition, through oxide and hydroxide formation, iron and aluminum can remove natural organic matter such as humic and fulvic acids from water and thus minimize the levels of toxic DBPs in drinking water. Within the scope of water treatment plants as used herein are municipal or regional water treatment facilities, a disposable tap water filter that has a service life of, for example, a few months; a part of a semi-permanent water purification/softening system for the entire home, that requires media replacement, for example, once a year; and an additional purification step for well water, as can be used, for example, in rural areas.

In one aspect, the system of the invention can be portable. Such a portable water treatment system can be used in households, in traveling, for camping or hiking, during natural disasters, and in developing countries where basic water treatment practices do not exist. Current practice is to use iodine or microfiltration in such settings. Unfortunately, iodine is not very effective at removing viruses and protozoa. Moreover, microfiltration is ineffective in removing viruses. A portable water treatment system can be any suitable size. In particular, it can be hand-held. A portable water treatment system can also be mounted on a vehicle, railroad car, or ship.

Incorporation of substantially zero-valent iron (and/or substantially zero-valent aluminum or other similar material) into new or existing filtration media and/or tank reactors can be used, for example, as follows: a) as a pre-disinfection process before chlorination or other disinfection treatment, to eliminate the need for storing liquid chlorine in water and wastewater treatment plants and other facilities, which can raise risks of accidental or deliberate release of chlorine (e. g., due to terrorist attack); b) to reduce the dosage and/or contact time of disinfectant (s) required to achieve desired removal of microorganisms and prevent re-growth during distribution, thus minimizing pathogens, DBP formation, and residual disinfectant levels in water simultaneously; c) to circumvent and/or prevent potential terrorist activities as zero-valent iron and other similar materials may be effective against many toxic chemicals and biological agents released to air or water by terrorists; d) to help to reduce or possibly completely eliminate chlorine use in water which would be useful to government agencies and utility companies seeking to meet drinking water standards.

Elemental iron can be found in anything containing iron metal, including but not limited to steel (or its derivatives, like nuggets, shots, grit, etc.), scrap iron, cast iron, iron sponge, powder, filings, and slugs. Aluminum containing material of any type, shape and form can also be used if desired for any reason. Elemental iron is in some cases preferred over $Fe^{++}$ and $Fe^{+++}$ compounds because its capacity to remove microbes and DBP precursors is renewed continuously through corrosion and thus it will last much longer without having to be replaced or rejuvenated as often. For example, elemental iron can remain active for as long as ten years in the field and more than one year in a laboratory column study, whereas $Fe^{++}$ and Fe oxides may cease to work quickly as surface sites are occupied, covered, or inactivated over time.

Similarly, for wastewater treatment, an active or passive treatment system involving elemental iron or aluminum may be used to remove viruses, bacteria, protozoa, other microbes, and/or DBP precursors from wastewater to meet the treatment or discharge requirement and to minimize the negative impact of wastewater discharge to the ecosystem. For groundwater applications, passive underground iron PRBs or active injection of iron particles or suspensions into the subsurface, for example, are two possible approaches to remove microorganisms such as viruses from groundwater and/or to prevent their migration in the subsurface. In these examples, such treatment (or pre-treatment) with elemental iron or aluminum may save the cost of disinfection (e. g., through use of less disinfectants and other chemicals) and at the same time reduce the formation of harmful DBPs associated with use of chlorine, ozone, or other disinfectants.

The present invention has several significant benefits, including better protection of public health from diseases related to water-borne and other pathogens and/or DBPs, cost savings due to lower overall disinfection cost, lower residual disinfectant level and reduced production of undesirable DBPs during water or wastewater treatment. In addition, the proposed iron/aluminum process has the following advantages:

(1) Cast or scrap iron is an industrial waste material and may be a readily available and inexpensive form of elemental iron (typically >90% iron content).

(2) Elemental iron and aluminum particles can have many years of service life without regeneration and can be used (among other processes) in a passive process, such as a gravity-fed treatment column or filter, to minimize maintenance and operational cost.

(3) Corrosion of iron and aluminum does not create any toxic by-products and therefore poses little threat to the environment and human health. In fact, when used for drinking water treatment, iron and aluminum corrosion products, such as $Fe^{++}$, $Fe^{+++}$, and $Al^{+++}$ ions, can serve as coagulants to improve the efficiency of water treatment (i. e., better removal of suspended solids from water) and reduce the chemical cost for coagulants, such as ferrous sulfate, ferric chloride, and aluminum sulfate.

(4) Depending on the amount of iron/aluminum used and the contact time, the treatment alone may achieve sufficient disinfection. Or, the proposed process may be combined with a subsequent and/or prior disinfection method such as UV irradiation, chlorination, ozonation, or chloramination to meet the desired treatment goal. In the latter case, an iron/aluminum pretreatment can lower the material and operational costs for disinfection and can also minimize the safety concerns associated with using chemical disinfectants.

By removing natural organic matter, well-known precursors of DBPs, and lowering the dosage of disinfectants used, the proposed iron/aluminum treatment also has an added advantage of reducing the potential of DBP formation and the toxicity of residual disinfectants. DBPs are toxic and/or carcinogenic compounds formed through reactions of DBP precursors (e. g., natural organic matter) and chemical disinfectants used in water and wastewater treatment processes (such as chlorine).

In accordance with the present invention, elemental iron and/or other elements alone or in combination are employed to remove and/or inactivate microorganisms from water or other media. The two viruses and the cast iron employed are merely exemplary. Similar results would also be achieved with other types of elemental iron and aluminum. In addition, a combination of iron and aluminum and/or other elements could be used. It is desirable in many embodiments if the amount of elemental iron or other microorganism-removing agent is from 0.01 to 99.99% by weight based on the total weight of material used for treatment of the media, such as based on the weight of sand, rock, gravel, and/or other filtration component particularly preferably from 1 to 99% by weight. In some embodiments, the present invention relates to a conduit such as a column filled with standard water filtration media (e. g., anthracite, sand, gravel, activated carbon, zeolite, clay, diatomaceous earth, garnet, ilmenite, zircon, charcoal, and/or ion exchange resin). Alternatively, the present invention could take any other desired form such as a continuous-flow, batch, or semi-batch mixed-tank reactor containing water to be treated, to which iron or aluminum is added to remove microorganisms and/or DBP precursors.

This invention preferably employs a device which utilizes a medium that contains elemental iron or aluminum as an active component in a batch, semi-batch, or flow-through column or tank system for the treatment of drinking water, wastewater, surface water, groundwater, backwash water, leachate, or any other liquid or gaseous streams containing microbial agents and/or DBP precursors. The device, which may be either portable or stationary, may comprise a column, conduit, cartridge, filter, barrier, tank, or another device or process (termed "device" hereafter) which utilizes a microorganism-removing agent. The device contains any microorganism-removing agent such as elemental iron or aluminum as an active treatment component and may also contain other constituents, such as sand or gravel, for functional, economic, or any other desired purposes (e. g., to minimize head loss, to prevent clogging, or to control pH). Water or air (or other material sought to be treated) is introduced into the device containing the microorganism-removing agent such as elemental iron or aluminum. After a sufficient contact time, which depends on factors such as system configuration, amount of microorganism-removing agent, mixing, and flow rate, microorganisms and/or DBP precursors are removed from the influent water or air by iron and/or aluminum particles. The treated water or air exiting the device (i. e., the effluent) will have a lower content of microorganisms and/or DBP precursors than the influent water. The viral content can be reduced by 50%. In a particular case, the viral content in water can be reduced using iron by about 97% to about 99% and even 99.999% or more in some cases. In the present invention, any flow velocity can be employed. The flow velocity when a column is employed is preferably from about 0.1 cm/h to about 10 m/min, particularly preferably at least about 1.0 cm/h. Any desired residence time can be employed. In some embodiments a residence time in the corrodible material is preferably at least about 0.1 second, particularly preferably from 1 second to 500 minutes, and even more preferably from 5 seconds to 60 minutes. In one aspect, the residence time is from about 2 minutes to about 30 minutes. The residence time can be about 5 minutes to about 20 minutes. In a particular aspect, the residence time is about 20 minutes. In another particular aspect, the residence time is about 8 minutes.

Figure 1:
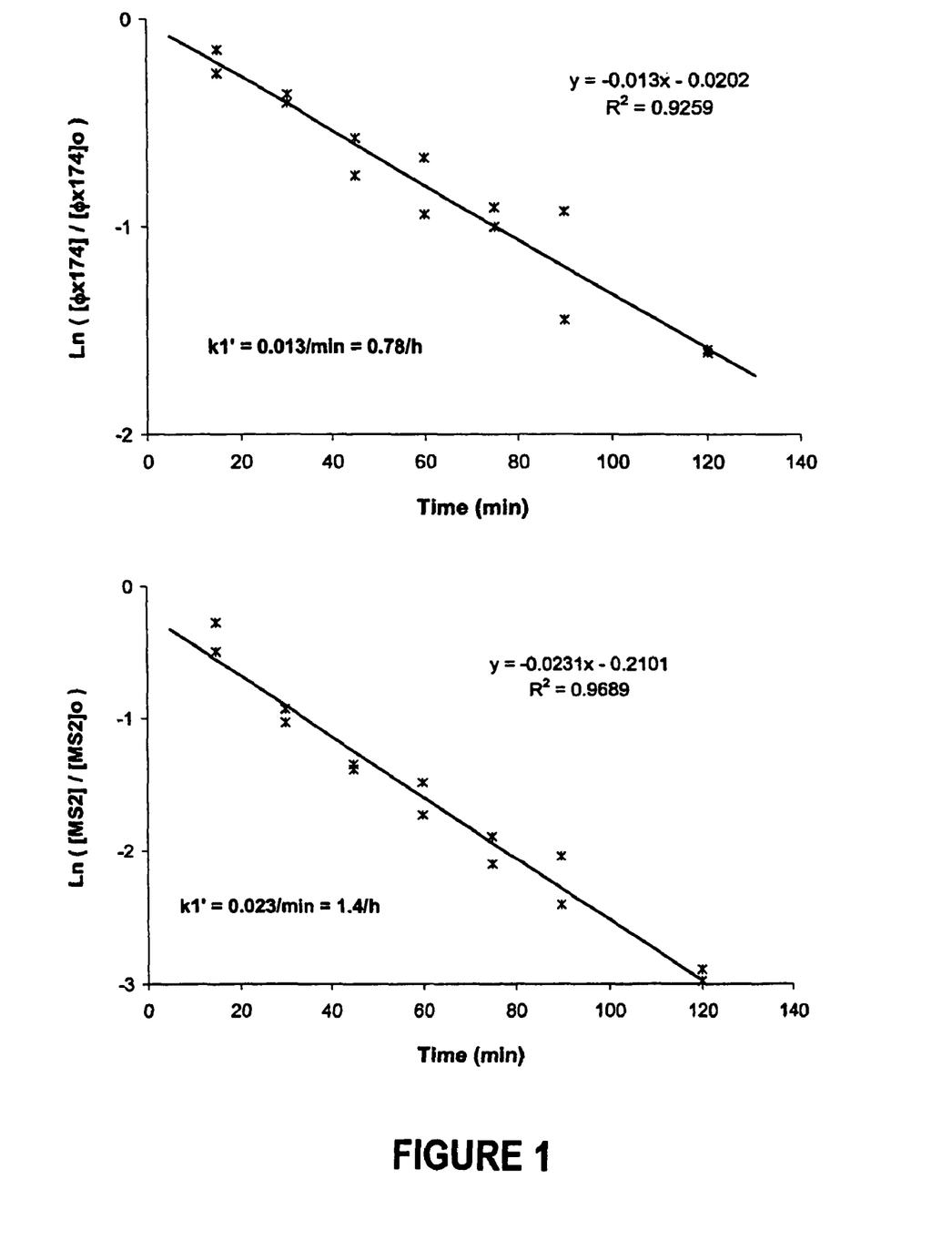
FIG. 1 shows the pseudo-first-order removal of the bacteriophages MS-2 and $\phi$X174 in AGW in batch reactors containing 1.0 g of Peerless™ iron granules. Initial virus concentrations were $\approx 10^5$ pfu/mL. The shaking speed was 20 rpm.

Column and batch experiments have been conducted using two viruses, to prove the concept and to demonstrate the effectiveness of elemental iron in removing microorganisms from water. The experimental setup and procedure had been developed and used previously by the inventors to study the transport of viruses in porous media (Jin, 1997, 2000; Chu et al., 2000; Chu et al., 2001). A schematic diagram of the experimental setup is shown in FIG. 1. Fritted stainless steel plates were placed at both ends of the columns to obtain a uniform flow distribution. A fraction collector was used to collect samples. All columns were packed wet to avoid trapping of gas bubbles. The solution was deoxygenated by nitrogen and degassed under vacuum to remove dissolved oxygen and other gases. Column performance and hydrodynamic properties were determined with bromide as a conservative tracer, which was quantified by a Dionex ion chromatograph. The column experiments were conducted in a cold room with temperature controlled at 4-6 C to avoid virus inactivation by high temperatures. A detailed description is set forth infra in the examples section.

Elemental iron or aluminum can remove and/or inactivate water-borne microorganisms such as viruses. When influent water containing microbes such as viruses and bacteria comes into contact with elemental iron particles (e. g., placed in a treatment column or filter medium), microorganisms can be removed from water continuously.

This invention can potentially be used to treat any liquid or gaseous media, and in particular, is adapted for use with drinking water, wastewater, surface water, backwash water, irrigation water, food processing water, ballast water, leachate, groundwater, other aqueous wastes, contaminated air, and off gases. For example, for water treatment plants producing drinking water, a treatment column, cartridge, or filter containing elemental iron (in the form of filings or granules of cast or scrap iron, for example) as an active component may be used to remove microorganisms and/or DBP precursors in the water. Similarly, for wastewater treatment, an active or passive treatment system involving elemental iron may be used to remove microbes and/or DBP precursors from wastewater prior to disinfection and/or effluent discharge. For groundwater applications, passive underground iron PRBs or active injection of iron particles or suspensions into the subsurface, for example, are two possible approaches to remove microorganisms in groundwater and/or reduce their migration in the subsurface. In these examples, such treatment (or pre-treatment) with elemental iron may save the cost of disinfection (e. g., through use of less disinfectants and other chemicals) and at the same time reduce the residual disinfectant level and the formation of harmful DBPs associated with use of chlorine, ozone, or other disinfectants.

Existing water disinfection methods involve use of strong oxidizing chemicals, such as chlorine (or hypochlorite), bromine, iodine, chloramines, chlorine dioxide, and ozone to kill microorganisms in water. Chlorine is the most commonly used disinfectant in the U.S. and many other countries, but it has been shown to be less effective for viruses and protozoa than for bacteria. These disinfectants, all of which are toxic chemicals and have many safety concerns, need to be stored or generated on-site and applied on a continuous basis. In addition, the process requires active control and laborious maintenance. Furthermore, other chemicals (e. g., hydrochloric acid, sodium hydroxide, sulfur dioxide, etc.) are needed to control the pH and/or neutralize excess disinfectants. Some disinfection methods, such as ozone and UV disinfection, are less flexible, more complex and difficult to operate, and require large initial capital investment. Finally, many of these chemical disinfectants can react with constituents, such as natural organic matter, in water and wastewater to produce significant levels of toxic or carcinogenic DBPs including trihalomethanes, haloacetic acids, and bromate.

In contrast, the invention differs from existing water and wastewater disinfection processes in that (1) it can be passive and long-lasting and requires little maintenance, (2) it does not involve use of hazardous chemicals, (3) it does not generate harmful (by) products, (4) it is less expensive than the existing chemical (oxidative) methods to disinfect water, and (5) it is flexible and involves low capital investment, and can be used as a stand-alone unit or added/retrofitted to existing treatment facilities.

EXAMPLES

The following non-limiting examples are intended to further illustrate the present disclosure.

Virus Selection and Assay. Two bacteriophages, MS-2 and φX174, were selected as model viruses because they have been used as surrogates for human enteric viruses in previous studies due to their structural resemblance to many human enteric viruses and their ease of use. MS-2 is an icosahedral single-stranded RNA phage with a diameter of 26.0 to 26.6 nm (Van Duin, 1988) and an isoelectric point ($pH_{iep}$) of 3.9 (Zerda, 1982). MS-2 was obtained from the American Type Culture Collection (ATCC 15597B1) and grown on bacterial lawns of E. coli (ATCC 15597). φX174 is a spherical single-stranded DNA phage with a diameter of 23 nm and a $pH_{iep}$ of 6.6 (Ackerman, 1987). It was grown on an E. coli host (ATCC 13706). Concentrations of infective φX174 and MS-2 particles were determined by the plaque-forming unit assay using the agar overlay method (Adams, 1959). Briefly, 1 mL of host culture and 1 mL of diluted virus sample were added to a trypticase soy agar (TSA) tube, and the mixture was poured onto a TSA plate. The plates were solidified for 15 min and placed in a 37° C. incubator for 5 h and 12 h for φX174 and MS-2, respectively. Viable virus concentration was determined by counting the plaques in the host lawn and reported as plaque-forming units per milliliter (pfu/mL). Only dilutions that resulted in 10 to 300 plaques per plate were accepted for quantification (i.e., the limit of quantification was set to be 10 pfu/plate for this study). All virus assays were performed in duplicates.

Iron and Sand. The zero-valent iron used for this study was commercial iron particles (ETI8/50) obtained from Peerless Metal Powders & Abrasive (Detroit, Mich.). The iron was used as received without pretreatment. The specific surface area of the Peerless iron was 1.67 $m^2/g$, as measured by the Brunauer-Emmett-Teller (BET) adsorption method with nitrogen. This value is within the range reported by other authors for Peerless™ iron (e.g., 1.50 $m^2/g$ by Alowitz and Scherer, 2002 and 2.53 $m^2/g$ by Su and Puls, 2003). In addition to zero-valent iron, the Peerless™ iron also contained magnetite, maghemite, and graphite, as determined by X-ray powder diffraction with CuKα radiation using a Philips/Norelco diffractometer. Accusand (Unimin, Le Sueur, Minn.) with the following particle size distribution was used for the column experiment: 9% of 0.1-0.25 mm, 69.8% of 0.25-0.5 mm, and 21.2% of 0.5-1.0 mm. The properties of Accusand have been well-characterized in a laboratory study Schroth et al., 1996. It consisted essentially of quartz with trace levels of organic matter and metal oxide coating. The sand was treated to remove metal ions and oxides using a citrate buffer solution containing 44.1 g/L of sodium citrate ($Na_2C_6H_5O_7 \cdot 2H_2O$) and 10.5 g/L of citric acid, as detailed in Chu et al., 2001. After the treatment, the iron content decreased from 32.5 mg iron/kg sand to below the detection limit (0.02 mg iron/kg sand), as determined by extraction with 0.05 M sodium dithionite ($Na_2S_2O_4$) and 0.4 M sodium citrate and quantification using inductively coupled plasma (ICP).

Artificial Groundwater. An artificial groundwater (AGW) was used as the background solution, which contained 0.075 mM of $CaCl_2$, 0.082 mM of $MgCl_2$, 0.051 mM of KCl, and 1.5 mM of $NaHCO_3$ (ionic strength≈2 mM). After autoclaving and vacuum degassing, the pH of the AGW was adjusted to 7.5 using 0.1 M NaOH or HCl prior to use.

Both batch and column experiments were conducted in a large refrigerator at 5±1° C. to avoid inactivation of the viruses due to high temperature.

Example 1

Batch Experiments. Batch experiments were conducted to study the kinetics of virus removal by Peerless™ iron particles. Stock solutions of φX174 and MS-2 were diluted in AGW to the desired titer (~/$10^5$ pfu/mL). Experiments were performed using 250-mL amber borosilicate bottles prepared in duplicates. Following addition of 1.0 g iron particles, the bottles were filled completely (free of headspace) with virus solution and sealed immediately with an open-hole screw cap and a Teflon-lined silicone septum (10/90 mil, Alltech, Deerfield, Ill.). Care was taken to prevent trapping of air bubbles during filling and capping of the bottles as viruses can be inactivated at the air-water interface (Thompson et al., 1998; Thompson et al., 1999). The sealed bottles were shaken end-over-end at 20 rpm in a refrigerator. At different elapsed times, 1.0 mL of virus-free AGW was injected into the bottle through a fully inserted 5.5" stainless steel side port needle (Popper & Sons, NY), and simultaneously a 1-mL sample was displaced through an inserted 2" stainless steel side port needle (Alltech). The different needle lengths were used to ensure spatial separation of injection and sampling points to prevent sample dilution. Side port needles were used to minimize damage to septa and avoid introduction of air. The 1-mL sample was analyzed immediately for viable virus concentration by the plaque assay.

To determine whether virus removal was due to reversible adsorption to iron or irreversible adsorption and inactivation, solution was discarded after the last sample was taken and 250 mL of 3% beef extract solution (BEX, pH 9.5) was added to the bottle to extract viruses from iron particles. BEX is a high-ionic strength enzyme digest of beef protein and has been shown to effectively detach viruses adsorbed to various surfaces (Gerba et al., 1984). The bottle was then shaken at 5° C. for 30 min and concentrations of viable viruses in BEX were measured. Controls (without iron) were set up in an identical fashion to assess any background adsorption and/or inactivation of the viruses during the experiment.

Results of Batch Experiments. FIG. 1 shows the removal of $\phi$X174 and MS-2 from the solution in batch reactors containing 1.0 g of iron particles. The aqueous concentrations of viable MS-2 and $\phi$X174 decreased continuously over two hours, and the removal appeared to follow first-order kinetics. In contrast, in the absence of iron, no removal of either virus was observed at 5° C. during the same time period. This indicates that both viruses were removed from solution by iron particles. Result of the BEX recovery test shows that only 0.13% of the MS-2 and 0.16% of the $\phi$X174 adsorbed were viable and could be recovered from the iron particles. Therefore, most of the viruses removed from solution were either irreversibly adsorbed or rendered non-infective. Using eq. 1, the first-order rate constants for MS-2 and $\phi$X174 removal at pH 7.5 were estimated to be 0.0231±0.0038 and 0.0130±0.0020 min$^{-1}$, respectively.

$$\ln[\text{virus}] = \ln[\text{virus}]_o - k_1 \cdot t \tag{1}$$

In eq. (1), [virus] is the infective virus concentration in solution at time t, [virus]$_o$ is the initial virus concentration measured before iron addition, and $k_1$ is the apparent first-order virus removal rate constant.

Because removal of virus from water by iron particles in a batch reactor involves multiple steps, the observed first-order rate constants may reflect the rate of any one of these processes or their combination: mass transfer of virus from bulk solution to the exterior surface of an iron particle, diffusion of virus in pores within an iron particle, and adsorption of virus to a surface site. Although kinetic data for the intra-particle diffusion and adsorption of viruses are not available, it is possible to estimate the external mass transfer rate constant ($k_{MT}$, s$^{-1}$), using the procedure described by Arnold et al. (1999). $k_{MT}$ is the product of mass transfer coefficient ($k_L$, m/s) and the ratio of particle geometric surface area to solution volume (a, m$^{-1}$). If external mass transfer is slow relative to the other processes, the overall rate constant ($k_1$) would be comparable to $k_{MT}$. Conversely, if another process is rate-limiting, $k_{MT}$ would be significantly larger than $k_1$.

The mass transfer between bulk solution and suspended particles in a mixed batch system is controlled largely by the velocity of the particles relative to the fluid; that is, the particles' terminal velocity. Using the semi-theoretical eq. (2) (Harriott, 1962) for mass transfer to spherical particles moving at their terminal velocity with a Reynolds number greater than 1, the minimum mass transfer rate coefficient ($k_L^*$) can be calculated, as shown below.

$$Sh = (k_L^* d_p / D_w) = 2 + 0.6 (Re)^{0.5} (Sc)^{0.33} = 2 + 0.6 (d_p u/v)^{0.5} (v/D_w)^{0.33} \tag{2}$$

In eq. (2), Sh, Re, and Sc are dimensionless Sherwood number, Reynolds number, and Schmidt number, respectively, $k_L^*$ is the minimum (uncorrected) mass transfer coefficient (m/s), $d_p$ is iron particle diameter (~5×10$^{-4}$ m), $D_w$ is the diffusion coefficient of the viruses in water (m$^2$/s), u is the terminal velocity of the iron particles (m/s), and v is the kinematic viscosity of water at room temperature (1.02E-6 m$^2$/s). Using a corrected Stokes' Law (Seinfeld et al., 1998), the terminal velocity of iron particles (u) was calculated to be 0.18 m/s, with a corresponding Re of 87. The $D_w$ values of the two viruses are expected to be similar because of their similar sizes. Using an assumed diameter of 23 nm for both viruses and either the Stoke-Einstein equation (Atkins, 1994) or an empirical equation proposed by Wilke and Chang (1955), $D_w$ was calculated to be 2.0×10$^{-11}$ m$^2$/s. The Sherwood and Schmidt numbers based on this $D_w$ are 5.4×10$^{-4}$ and 206, respectively. $k_L^*$ can then be calculated to be 7.8×10$^{-6}$ m/s using eq. (2). Harriott (1962) suggested that, in a mildly stirred batch system without an impeller, the actual mass transfer coefficient ($k_L$) is likely to be 1.2 to 1.5 times $k_L^*$. Because 1.5 was used as a correction factor in an earlier study to estimate $k_L$ and a good agreement with experimental data was observed (Arnold et al., 1999), we used 1.5 to obtain an estimated $k_L$ of 1.2×10$^{-5}$ m/s. Finally, based on the iron mass (1.0 g) and liquid volume (250 mL) used, an assumed spherical particle geometry, and an estimated nominal density of 6,500 kg/m$^3$ for the iron, we calculated the geometric surface area-to-solution volume ratio (a) to be 7.4 m$^{-1}$. Therefore, the external mass transfer rate constant $k_{MT} = k_L a = 8.7 \times 10^{-5}$ s$^{-1}$, or 0.0052 min$^{-1}$.

This calculated $k_{MT}$ value is a factor of 2 to 4 lower than the apparent removal rate constants for MS-2 and $\phi$X174 (FIG. 1). Since $k_1$ must be smaller than or equal to $k_{MT}$, this underestimation is most likely due to the assumptions and uncertainties involved in our calculations, especially those related to the estimation of diffusivity $D_w$ (since viruses are much larger and more massive than dissolved molecules) and surface area concentration a (which was probably underestimated since the iron particles were not spherical). Nonetheless, the estimated $k_{MT}$ argues that external mass transfer was probably the rate-limiting process that controlled the overall rate of virus removal from solution in our batch reactors.

Example 2

Column Experiments. In one column experiment that we conducted to demonstrate the utility of the invention, a thin layer (~3 mm) of Peerless™ iron was sandwiched into a column (3.5 cm i. d.×8 cm length) packed with 8-cm Accusand sand, which had been treated to remove any trace metal oxides. An input solution containing ~10 plaque-forming units per liter ("pfu/L," a measure of the concentration of viable or infective viruses in solution) of MS2 and $\phi$X174, respectively, was pumped into the column at a flow velocity of 2.05 cm/h. This gives a residence time of 8.8 min in the iron layer.

Effluent samples were collected with a fraction collector and analyzed for both viruses. In the control experiment, only treated (oxide-free) sand was used to pack the column and the experiment was run as described above. A 3% beef extract solution (pH 9.5) was used to elute the columns at the end of experiments to recover viable viruses and determine if the viruses retained were due to reversible sorption or inactivation. The column was packed wet by filling it partially with artificial ground water (AGW, pH 7.5, ionic strength 2.0 mM) to avoid trapping of air bubbles and ensure packing uniformity. The AGW contained 0.075 mM CaCl2, 0.082 mM MgCl2, 0.051 mM KCl, and 1.5 mM NaHCO3. In this example a solution containing approximately 108 pfu/L of both MS2 and φX174 was introduced into the column as a step input, using a peristaltic pump at a flow velocity of 2.05 cm/h. This gave a residence time of 8.8 min in the iron section based on the porosity of the Peerless™ iron. Effluent samples were collected with a fraction collector and analyzed for both viruses using the standard procedures according to Adams, 1959, detailed infra. In another experiment, only treated (iron oxide-free) sand was used to pack the column and the virus removal experiment was repeated as described above. A 3% beef extract solution (pH 9.5) was used to elute the columns at the end of each experiment to obtain a mass balance for the viruses and to determine whether the viruses were removed due to reversible sorption or irreversible sorption/inactivation.

Figure 2:
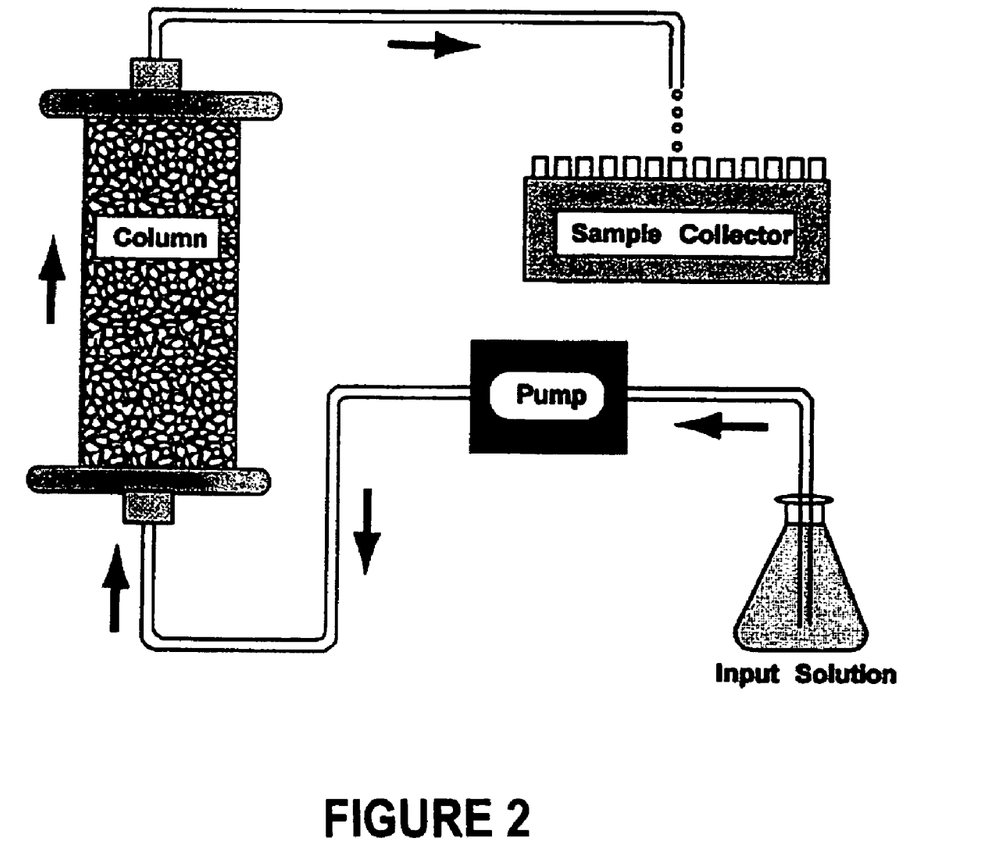
FIG. 2 illustrates a schematic of a suitable experimental column setup for use in connection with the present invention.
Figure 3:
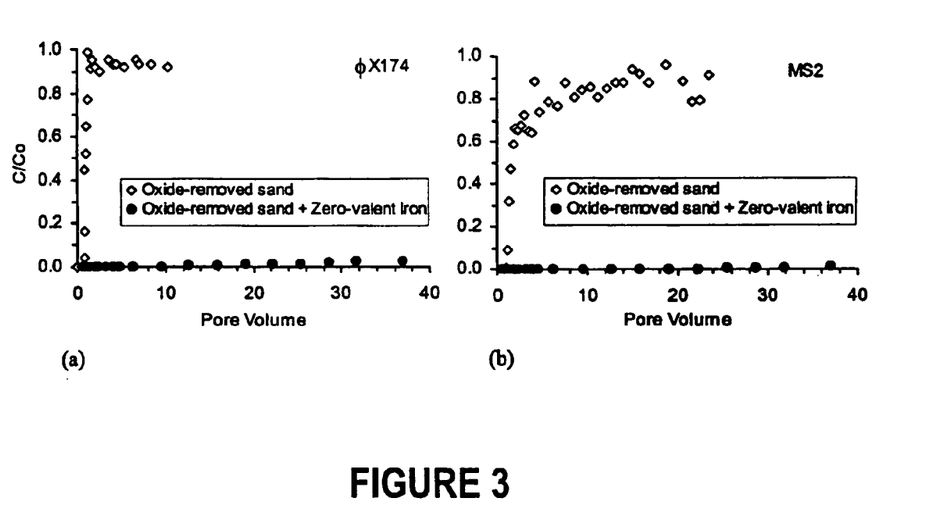

Breakthrough curves of φX174 and MS2 from the clean (oxide-free) sand column and the sand column containing 3 mm of Peerless iron are shown in FIG. 2. As the data show, in the cleaned (oxide-free) sand column without elemental iron, the viruses broke through completely and little removal was observed. In contrast, with only 3 mm of Peerless™ iron, greater than 99% and 97% removal from the AGW was achieved for MS2 and (φX174, respectively. These removal efficiencies were sustained over about 40 pore volumes, indicating that elemental iron can continuously remove viruses from the incoming water. Based on the mass recovery results from beef extract elution, the observed (97-99%) removal of both viruses by elemental iron was predominantly (approximately 90%) due to inactivation or irreversible sorption, and only about 10% was due to reversible sorption.

These results clearly demonstrate that even a very thin layer (3 mm) of commercial cast iron was able continuously to remove a large fraction of viruses from contaminated water. For large-scale treatment systems, the removal efficiency can be increased as desired by increasing the contact time of viruses with iron particles. This may be achieved by increasing the contact time through one of the following or their combinations: increasing the amount of iron used, decreasing the iron particle size, or reducing the water flow rate (e. g., by increasing the column's cross-section area).

Example 3

Figure 4:
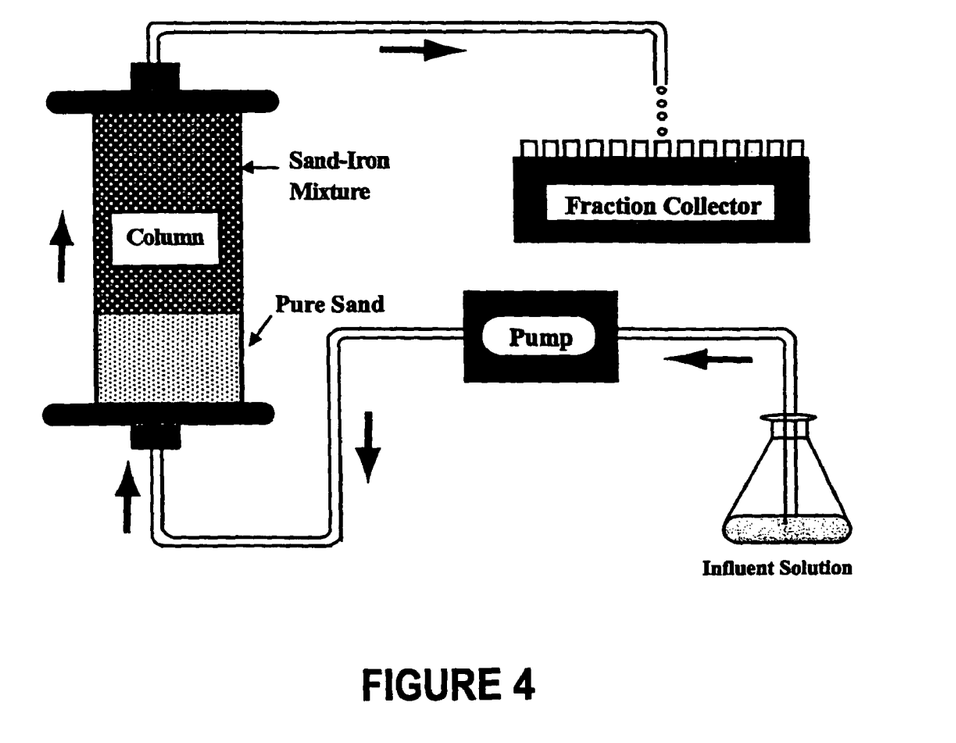
FIG. 4 is a schematic diagram of column experiment setup.

Column Experiments. Further column experiments were conducted to evaluate the effectiveness of iron to remove viruses from water under continuous, saturated flow conditions and over an extended operation time. The experiment was performed using a setup (FIG. 4) similar to that in Example 2. In brief, two identical glass chromatography columns having a 3.8-cm i.d. and a 10-cm length were used. The control column was wet-packed with oxide-removed sand by pouring sand into an AGW-filled column at 1-cm increments while stirring with a glass rod to remove any attached air bubbles. The iron column was packed in a similar manner with 3 cm of oxide-removed sand followed by 7 cm of 1:1 (v/v) mix of oxide-removed sand and Peerless™ iron particles. The iron mass in the packed iron column was approximately 150 g.

Each column was flushed with 10 pore volumes (PV) of autoclaved and degassed AGW at a flow rate of 0.5 mL/min. The flow rate was then increased to 1 mL/min and flushing was continued for another hour to establish a steady-state flow condition prior to virus introduction. This procedure gives a residence time of 41 min in the sand column and 58 min in the iron column. Given the iron content of 35% by volume, the effective contact time with iron in the iron column was 20 min.

For each pulse test, a solution containing ~$10^5$ pfu/mL each of φX174 and MS-2 and 50 ppm of bromide was introduced into both columns at approximately 1 mL/min for 5 PVs using a peristaltic pump. Effluent samples from both columns were collected in 6-mL tubes at 5-min intervals (i.e., 5 mL sample/tube) using a fraction collector. After the 5-PV slug input, the influent was switched back to the virus-free background solution (sterilized, degassed, and pH-adjusted AGW), and effluent samples were collected for another 5 PVs. Pumping of the background solution was continued at ~1 mL/min for 10 days (>320 PVs) before the second pulse test was conducted. The effluent concentrations of the viruses and bromide were determined by the plaque assay and ion chromatography (Doinex, Sunnyvale, Calif.), respectively.

Figure 5:
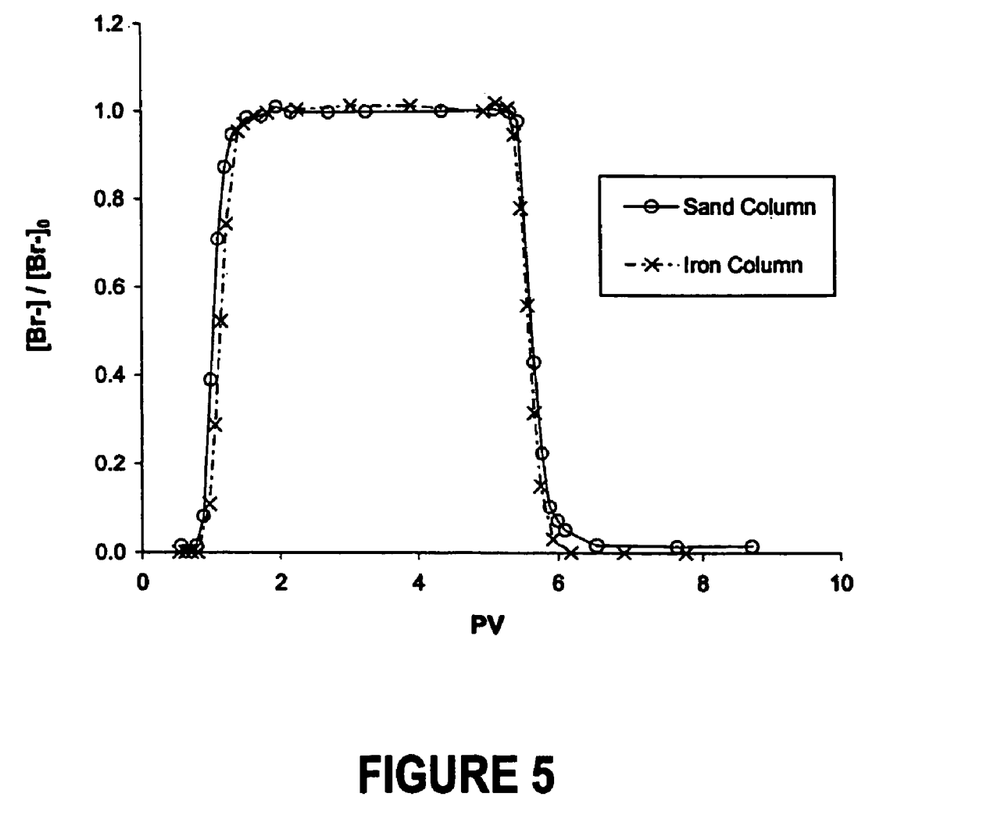
FIG. 5 illustrates breakthrough curves of bromide tracer from columns packed with oxide-removed sand only and oxide-removed sand plus iron granules.
Figure 6:
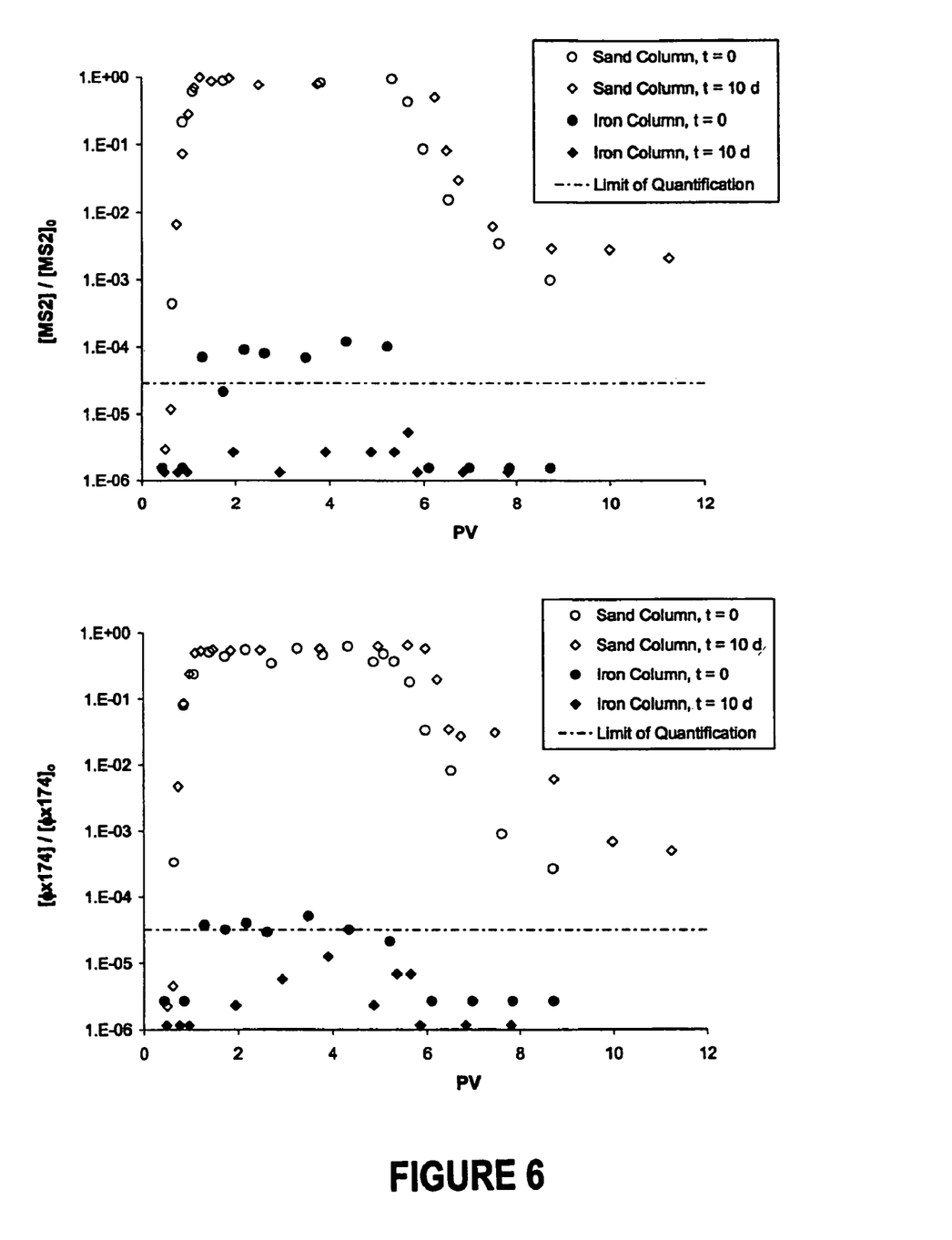
FIG. 6 shows breakthrough curves of MS-2 and $\phi$X-174 from sand and iron columns in two pulse tests conducted shortly after packing (t=0) and after passage of over 320 PVs of AGW (t=10 d). The limit of quantification corresponds to 10 pfu/plate of undiluted sample. Note that when a sample produced zero plaque, a calculated virus concentration corresponding to 1 pfu/plate was assigned for plotting purposes. These data points should be regarded as upper limits of the actual virus concentrations in the samples.

Results of Further Column Experiments. The bromide breakthrough curves from the control column and the iron column are shown in FIG. 5. The two breakthrough curves essentially overlap, indicating that the water flow conditions in both columns are very similar. These curves are well-described by the equilibrium convection-dispersion equation (Toride, 1995), indicating that there was no physical non-equilibrium in either column. Using the bromide breakthrough data, we calculated the pore volumes of the sand and iron columns to be 41 and 58 mL, respectively.

Thus, the batch experiments show that removal of two bacteriophages by commercial zero-valent iron was rapid, with rates approaching the limit of external mass transfer. The removal appeared to be largely due to irreversible adsorption or inactivation of the viruses. The column studies demonstrate that in a flow-through system, over 5-log removal of both viruses can be achieved within an effective contact time with iron of 20 min. Furthermore, the column data suggest that, as water flowed through the iron column, new iron (oxyhydr)oxides were formed continuously to serve as new adsorption sites, and the capacity of iron to remove waterborne viruses could be sustained or even improved.

Each of the references described above and/or cited below are incorporated by reference herein in its entirety for all useful purposes. These references include the following:

While there is shown and described certain specific structures embodying the invention, it will be manifest to those skilled in the art that various modifications and rearrangements of the parts may be made without departing from the spirit and scope of the underlying inventive concept and that the same is not limited to the particular forms herein shown and described.

As used herein and in the following claims, terms such as "a", "the" and so on can connote the singular or plural of terms that follow.

REFERENCES

Abbaszadegan, M., P. W. Stewart, M. W. LeChevallier, J. S. Rosen. and C. P. Gerba. 1998/1999. Occurrence of Viruses in Ground Water in the United States. American Water Works Association Research Foundation, Denver, Colo.

Ackerman, H. W., and M. S. Dubow. 1987. Viruses of Prokaryotes. In: CRC Press. Boca Raton, Fla. 2:190-191.

Adams, M. H. 1959. Bacteriophages. Interscience Publishers, New York. P. 1-4.

Alowitz, M. J.; Scherer, M. M. Kinetics of nitrate, nitrite, and Cr(VI) reduction by iron metal. 2002. *Environ. Sci. Technol.* 36: 299-306.

Arnold, W. A.; Ball, W. P.; Roberts, A. L. Polychlorinated ethane reaction with zero-valent zinc: pathways and rate control. 1999, *J. Contam. Hydrol.* 40: 183-200.

Atkins, P. W. *Physical Chemistry*, 5th ed., W.H. Freeman, New York, 1994.

Amonette, J. C. and Zelazny, L. W. 1994. Quantitative methods in soil mineralogy. Soil Sci. Soc. Am. Misc. Publ., Soil Sci. Soc. Am., Madison, Wis.

Bull, R. J., Gerba, C. P., and Trussell, R. R. 1990. Evaluation of the health risks associated with disinfection. CRC Crit. Rev. Environ. Control. 20: 77-113.

Chu, Y. Jin, Y. and Yates, M. V. 2000. Virus transport through saturated sand columns as affected by different buffer solutions. J. Environ. Qual. 29: 1103-1110.

Chu, Y.; Jin, Y.; Flury, M.; and Yates, M. V. 2001. Mechanisms of virus removal during transport in unsaturated porous media. Water Resour. Res. 37: 253-263.

Chu, Y., Y. Jin, and M. V. Yates. 2000. Virus transport through saturated columns as affected by different buffer solutions. J. Environ. Qual. 29(4): 1103-1110.

EnviroMetal Technologies, Inc. (ETI) web site, 2005, http://www.eti.ca.

Farrell, J., Wang, J., O'Day, P. and Conklin, M. 2001. Electrochemical and Spectroscopic Study of Arsenate Removal from Water Using Zero-Valent Iron Media. Environ. Sci. Technol. 35: 2026-2032.

Gerba, C. P., and Goyal, S. M. 1981. Quantitative assessment of the adsorption behavior of viruses to soils. Environ. Sci. Technol. 15:940-944.

Gerba, C. P.; Marzouk, Y.; Manor, Y.; Idelovitch, E.; Vaughn, J. M. Virus removal during land application of wastewater: a comparison of three projects. 1984, *Future of Water Reuse*. AWWARF, Denver, Colo. 3, 1518-1529.

Gerba, C. P.; Rose, J. B. 1990. Viruses in source and drinking water. In: McFeters G. A. (Ed.), Drinking Water Microbiology: Progress and Recent Developments. Springer, N.Y., pp. 380-396.

Goyal, S. M.; Keswick, B. H; Gerba, C. P. 1984. Viruses in groundwater beneath sewage irrigated cropland. Water Res. 18, 299-302.

Gu, B., Schmitt, J., Chen, Z., Liang, L., McCarth, J. F. 1994, Environ. Sci. Technol. 28, 38-46.

Hancock, C. M., Rose, J. B. and Callahan, M. 1998, *Crypto* and *Giardia* in U.S. groundwater, J. Am. Water Works Assoc. 90, 58-61.

Harriott, P. Mass transfer to particles suspended in agitated tanks. 1962, *AIChE*, 8, 93-101.

Holzalski, R. M., Zhang, L., Arnold, W. A. 2001, Reduction of Haloacetic Acids by Fe(0); Implications for Treatment and Fate, Environ. Sci. Technol, 35, 2258-2263.

Jarvis, P. Jefferson, B., Parsons, S. A. 2005, How the Natural Organic Matter to Coagulant Ratio Impacts Floc Structural Properties, Environ. Sci. Technol., 39, 8919-8924.

Jensen, J. S. and Helz, G. R. 1998. Rates of reduction of N-chlorinated peptides by sulfite: relevance to incomplete dechlorination of wastewaters. Environ. Sci. Technol., 32, 516-522.

Jin, Y.; Yates, M. V.; Thompson, S. S.; Jury, W. A. 1997. Sorption of viruses during flow through saturated sand columns. Environ. Sci. Technol., 31, 548-555.

Jin, Y.; Chu, Y.; Li, Y. 2000. Virus removal and transport in saturated and unsaturated sand columns. J. Contam. Hydrol. 43, 111-128.

Jin, Y. and Flury, M. 2002. Fate and transport of viruses in porous media. Adv. Agron. 77: 39-102.

Kim, B. J., D. K. Cha, P. C. Chiu, and S. Y. Oh. 2002. A Process/System for Treating Pink Water Using Elemental Iron and Fenton Reaction. Patent pending.

Korich, D. G., Mead, J. R., Madore, M. S., Sinclair, N. A. and Sterling, C. R., 1990, Effects of ozone, chlorine dioxide, chlorine, and monochloramine on *Cryptosporidium parvum* oocyst viability. Appl. Environ. Microbiol. 56, 1423-1428.

Kramer, M. N., B. L. Herwaldt, G. F. Craun, R. L. Calderone, D. D. Juranek. 1996. Water-bone diseases: 1993 and 1994. J. Amer. Water Works Assn. 88: 66-80.

Kunze, G. W. and Dixon, J. B. 1986. Pretreatment of mineralogical analysis. In Klute, A (ed.), *Methods of Soil Analysis. Part 1. Physical and Mineralogical Analysis*. Soil Sci' Soc. Am., Madison, Wis. Pp 91-100.

Lisle, J. T. and Rose, J. B. 1995, *Cryptosporidium* contamination of water in the USA and UK: a mini-review, J. Water Supply Res. Technol. 44, 103-105.

MacCrehan, W. A.; Jensen, J. S. and Helz, G. R. 1998. Detection of sewage organic chlorination products that are resistant to dechlorination with sulfite. Environ. Sci. Technol., 32, 3640-3645.

McMurry, S. W., Coyne, M. S. and Perfect, E. 1998. Fecal coliform transport through intact soil blocks amended with poultry manure. J. Environ. Qual. 27: 86-92.

Mead, P. S., Slutsker L, Dietz V. et al. 1999. Food-related illness and death in the United States. Emerg. Infect. Dis, Vol. 5, No. 5.

Melitas, N, Conklin, M. and Ferrell, J. 2002. Electrochemical Study of Arsenate and Water Reduction on Iron media Used for Arsenic Removal from Potable Water. Environ. Sci. Technol. 36: 3188-3193.

Melitas, N., Wang, J., Conklin, M., O'Day, P. and Ferrell, J. 2002. Understanding Soluble Arsenate Removal Kinetics by Zerovalent Iron Media. Environ. Sci. Technol. 36: 2074-2081.

Moore, B. E., Taylor, D. H., Sturman, L. S., Reddy, M. M., and Fuhs, G. W. 1981. Poliovirus adsorption by 34 minerals and soils. Appl. Environ. Microbiol. 42: 963-975.

Murray, J. P., and Laband, D. J. 1979. Degradation of poliovirus by adsorption on inorganic surfaces. Appl. Environ. Microbiol. 37: 480-486.

Odziemkowski, M. S., Schuhmacher, T. T., Gillham, R. W. and Reardon, E. J. 1998. Mechanism of Oxide Film Formation on Iron in Simulating Groundwater Solutions: Raman Spectroscopic Studies. Corr. Sci. 40: 371-389.

Oh, S. Y, Chiu, P. C., Kim B. J. and Cha, D. K. 2003. Enhancing Fenton Oxidation of TNT and RDX through Pretreatment with Zero-Valent Iron. Water Res. 37: 4275-4283.

Payment, P.; Armon, R. 1989. Virus removal by drinking water treatment processes. CRC Crit. Rev. Environ. Control 19, 15-31.

Payment P., Siemiatycki J., Richardson L. 1997. A prospective epidemiological study of gastrointestinal health effects due to the consumption of drinking water. Int. J. Environ. Health Res., 7: 5-31.

Payment P., Richardson L., Siemiatycki J. et al. 1991. A randomized trial to evaluate the risk of gastrointestinal disease due to consumption of drinking water meeting currently accepted microbiological standards. Am. J. Public Health, 81: 703-708.

Penrod, S. L., T. M. Olson, and S. B. Grant. 1996. Deposition kinetics of two viruses in packed beds of quartz granular media. Langmuir. 12: 5576-5587.

Perey, J. R., Chiu, P. C., Huang C. P. and Cha, D. K. (2002) Zero-valent Iron Pretreatment for Enhancing Biodegradability of Azo Dyes. Water Environ. Res., 74: 221-225.

Plewa, M. J., Wagner, E. D., Richardson, S. D., Thruston, A. D., Jr., Woo, Y.-T., McKague, A. B. 2004, Chemical and Biological Characterization of Newly Discovered Iodoacid Drinking Water Disinfection Byproducts. Environ. Sci. Technol., 38: 4713-4722.

Remediation Technologies Development Forum (RTDF) web site, Technical Documents, 2003. http://www.rtdf.org.

Rosenberger, J. K., Olsen, N. O., and van der Heide, L. 1998. Viral arthritis/tenosynovitis and other reovirus infections. In Swayne, D. E. (ed.), A Laboratory Manual for the Isolation and Identification of Avian Pathogens, 4 Edition, American Association of Avian Pathologists, Kennett Square, Pa., pp. 207-210.

Ryan, J. N., R. W. Harvey, D. Metge, M. Elimelech, T. Navigato, and A. P. Pieper. 2002. Field and laboratory investigations of inactivation of viruses (PRD1 and MS2) attached to iron oxide-coated quartz sand. Environ. Sci. & Technol. 36: 2403-2413.

Sagripanti., J. L. 1992. Metal-based formulations with high microbial activity. Appl. Environ. Microbiol. 59: 3157-3162.

Sagripanti., J. L., Routson, L. B., and Lytle, C. D. 1993. Virus inactivation by copper or iron ions alone and in the presence of peroxide. Appl. Environ. Microbiol. 59: 4374-4376.

Seinfeld, J. H.; Pandis, S. N. *Atmospheric Chemistry and Physics*, John Wiley & Sons, New York, 1998.

Su, C.; Puls, R. W. 2003. In situ remediation of arsenic in simulated groundwater using zerovalent iron: laboratory column tests on combined effects of phosphate and silicate. *Environ. Sci. Technol.* 37, 2582-2587.

Schroth, M. H.; Ahearn, S. J.; Selker, J. S.; Istok, J. D. 1996. Characterization of miller-similar silica sand for laboratory hydrologic studies. *Soil Sci. Soc. Am. J.* 60, 1331-1339.

Toride, N.; Leji, F. J.; van Genuchten, M. T. 1995. The CXTFIT code for estimating transport parameters from laboratory or field tracer experiments, Version 2.1, *Res. Rep.* 137, U.S. Salinity Lab, Riverside, Calif.

United States Environmental Protection Agency, 1989a. Drinking water; national primary drinking water regulations; filtration, disinfection; turbidity, *Giardia lamblis*, viruses, *Legionella*, and heterotrophic bacteria; final rule. FR 54: 27486. (Jun. 29, 1989) USEPA, Washington, D.C.

United States Environmental Protection Agency, 1989b. Drinking water; national primary drinking water regulations; total coliforms (including fecal coliforms and *E. coli*); final rule. FR 54: 27544. (Jun. 29, 1989) USEPA, Washington, D.C.

United States Environmental Protection Agency, 1990. Reducing risk: setting priorities and strategies for environmental protection. Appendix B: report of the Human Health Subcommittee. USEPA Science Advisory Board, SAB-EC-90-021B, Washington, D.C.

United States Environmental Protection Agency, 2000. National primary drinking water regulations: Ground water rule; Proposed rule, Federal Register 65, 30194-30274, USEPA, Washington, D.C.

U.S. Environmental Protection Agency, Field Applications of In Situ Remediation Technologies: Permeable Reactive Barriers, Washington, D.C., January, 2002a.

U.S. Environmental Protection Agency, Research Brief: Long-term Performance of Permeable Reactive Barriers Using Zero-Valent Iron: An Evaluation at Two Sites. EPA/600/S-02/001, Cincinnati, Ohio, March, 2002b.

Vaughn, J. M.; Landry, E. F.; Baranosky, L. J.; Beckwith, C. A.; Dahl, M. C.; Delihas, N. C. 1978. Survey of human virus occurrence in wastewater-recharged groundwater on Long Island. Appl. Environ. Microbiol. 36, 47-51.

Vanduin, J. 1988. The single-stranded RNA bacteriophages. In R. Calendar (ed.) The Bacteriophages. Plenum, N.Y. 1:

Vidic, R. D. Permeable Reactive Barriers: Case Study Review, GWRTAC Technology Evaluation Report, TE-01-01, November, 2001.

Wilke C. R.; Chang, P. 1955. Correlation of diffusion coefficients in dilute solutions. *AIChE*, 1, 264-270.

Yates, M. V., C. P. Gerba, and L. M. Kelly. 1985. Virus persistence in groundwater. Appl. Environ. Microbiol. 49: 778-781.

Zerda, K. S. 1982. Adsorption of viruses to charge-modified silica. Ph.D. diss. Baylor Coll. of Medicine, Houston, Tex.

What is claimed is:

1. A disinfection system for reducing viruses in water by at least 50%, said system comprising
    either a conduit or a container packed with filtration media and only one microorganism-removing agent;
    wherein said only one microorganism-removing agent comprises particles of an element with an oxide, hydroxide, and/or oxyhydroxide coating having positively charged surface sites on said particles' surface through corrosion in water;
    wherein said element is selected from the group consisting of zero valent iron and zero valent aluminum;
    wherein said filtration media comprises at least one of anthracite, sand, gravel, activated carbon, zeolite, clay, diatomaceous earth, garnet, ilmenite, zircon, charcoal, and ion exchange resin; and
    wherein said only one microorganism-removing agent is mixed with said filtration media in an amount effective to remove said viruses.

2. A system according to claim 1, wherein said only one microorganism-removing agent is in contact with water to be treated for a time of about 0.1 second or more.

3. A system according to claim 1, wherein said system is portable.

4. A system according to claim 1, wherein said system is stationary.

5. A disinfection system as recited in claim 1, wherein said system is capable of reducing said viruses by at least about 97%.

6. A disinfection system as recited in claim 1, wherein said system is capable of reducing said viruses by at least about 99%.

7. A disinfection system as recited in claim 1, wherein said system is capable of reducing said viruses by at least about 99.9%.

8. A disinfection system as recited in claim 1, wherein said system is capable of reducing said viruses by at least about 99.99%.

9. A disinfection system as recited in claim 1, wherein said system is capable of reducing said viruses by at least about 99.999%.

10. A disinfection system as recited in claim 5, 6, 7, 8, or 9, wherein at least 90% of the viruses removed are removed by inactivation or irreversible sorption.

11. A disinfection system as recited in claim 1, wherein the weight percent content of said only one microorganism-removing agent is in the range of from about 1% to about 54%.

12. A disinfection system as recited in claim 1, wherein the weight percent content of said only one microorganism-removing agent is in the range of from about 8% to about 54%.

13. A disinfection system as recited in claim 1, wherein the weight percent content of said only one microorganism-removing agent is in the range of from about 54% to about 99.99%.

* * * * *